(12) United States Patent
Sackett et al.

(10) Patent No.: US 8,167,882 B2
(45) Date of Patent: May 1, 2012

(54) MINIMALLY INVASIVE BONE MILLER APPARATUS

(75) Inventors: Samuel G. Sackett, Fort Wayne, IN (US); Brian P. Johnson, Jackson, MS (US); Samuel B. Owen, Jackson, MS (US); Larry G. McCleary, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 796 days.

(21) Appl. No.: 12/241,418

(22) Filed: Sep. 30, 2008

(65) Prior Publication Data

US 2010/0082031 A1    Apr. 1, 2010

(51) Int. Cl.
*A61B 17/16*     (2006.01)

(52) U.S. Cl. ............................................ 606/79; 606/80

(58) Field of Classification Search .............. 606/79–85, 606/86 R, 96, 98, 167, 180; 409/215
See application file for complete search history.

(56) References Cited

U.S. PATENT DOCUMENTS

| | | | |
|---|---|---|---|
| 650,795 A * | 5/1900 | Maxwell | 74/385 |
| 1,029,402 A * | 6/1912 | Ritter | 409/144 |
| 3,177,507 A * | 4/1965 | Becker et al. | 470/86 |
| 3,633,583 A | 1/1972 | Fishbein | |
| 3,810,312 A | 5/1974 | Carson | |
| 4,004,581 A | 1/1977 | Heimke et al. | |
| 4,116,200 A | 9/1978 | Braun et al. | |
| 4,473,070 A | 9/1984 | Matthews | |
| 4,658,808 A | 4/1987 | Link | |
| 4,716,894 A | 1/1988 | Lazzeri | |
| 4,738,256 A | 4/1988 | Freeman et al. | |
| 4,777,942 A | 10/1988 | Frey et al. | |
| 4,917,530 A | 4/1990 | Engelhardt | |
| 4,969,911 A | 11/1990 | Greene | |
| 5,002,578 A | 3/1991 | Luman | |

(Continued)

FOREIGN PATENT DOCUMENTS

DE    3538654 A1    4/1987

(Continued)

OTHER PUBLICATIONS

English translation of WO 3015642.*

(Continued)

*Primary Examiner* — Thomas C. Barrett
*Assistant Examiner* — Christian Sevilla

(57) ABSTRACT

A miller assembly for creating a cavity in a bone. The cavity has a cross section which has a generally triangular profile having a first side generally parallel with an axis of the bone and a second side forming an acute angle with the first side, and is contiguous with a pre-existing conical cavity in the bone. The miller assembly includes a cutter and a frame for carrying the cutter. The frame includes a connection portion having a longitudinal axis and a cutter mount for mounting the cutter at a first angle approximating the acute angle with respect to the longitudinal axis of the connection portion. The cutter mount extends at the first angle from the longitudinal axis of the connection portion and is configured to receive a portion of the cutter and maintain the received cutter oriented at the first angle during rotation. The frame further includes a handle configured to form a portion of a drive joint for coupling the frame to a drill, the handle having a longitudinal axis. The longitudinal axis of the handle is coincident with the longitudinal axis of the frame.

10 Claims, 6 Drawing Sheets

U.S. PATENT DOCUMENTS

| | | |
|---|---|---|
| 5,002,581 A | 3/1991 | Paxson |
| 5,015,255 A | 5/1991 | Kuslich |
| 5,047,033 A | 9/1991 | Fallin |
| 5,053,037 A | 10/1991 | Lackey |
| 5,100,407 A | 3/1992 | Conrad |
| 5,135,529 A | 8/1992 | Paxson |
| 5,171,244 A | 12/1992 | Caspari et al. |
| 5,192,283 A | 3/1993 | Ling et al. |
| 5,197,989 A | 3/1993 | Hinckfuss |
| 5,201,882 A | 4/1993 | Paxson |
| 5,207,680 A | 5/1993 | Dietz |
| 5,228,459 A | 7/1993 | Caspari et al. |
| 5,263,498 A | 11/1993 | Caspari et al. |
| 5,304,181 A | 4/1994 | Caspari et al. |
| D346,979 S | 5/1994 | Stalcup et al. |
| 5,336,226 A | 8/1994 | McDaniel |
| 5,342,363 A | 8/1994 | Richelsoph |
| 5,344,423 A | 9/1994 | Dietz et al. |
| 5,370,706 A | 12/1994 | Bolesky |
| 5,372,209 A | 12/1994 | Raihert |
| 5,387,218 A | 2/1995 | Meswania |
| 5,395,376 A | 3/1995 | Caspari et al. |
| D357,315 S | 4/1995 | Dietz |
| 5,403,320 A | 4/1995 | Luman et al. |
| 5,415,659 A | 5/1995 | Lee |
| 5,468,243 A | 11/1995 | Halpern |
| 5,470,336 A | 11/1995 | Ling et al. |
| 5,474,559 A | 12/1995 | Bertin et al. |
| 5,486,180 A | 1/1996 | Dietz et al. |
| 5,496,324 A | 3/1996 | Barnes |
| 5,507,815 A | 4/1996 | Wagner et al. |
| 5,507,824 A | 4/1996 | Lennox |
| 5,507,830 A | 4/1996 | DeMane |
| 5,507,833 A | 4/1996 | Bohn |
| 5,527,316 A | 6/1996 | Stone |
| 5,534,005 A | 7/1996 | Tokish, Jr. et al. |
| 5,540,694 A | 7/1996 | DeCarlo, Jr. et al. |
| 5,569,255 A | 10/1996 | Burke |
| 5,593,411 A | 1/1997 | Stalcup et al. |
| 5,601,563 A | 2/1997 | Burke et al. |
| 5,601,567 A | 2/1997 | Swajger |
| 5,607,269 A | 3/1997 | Dowd et al. |
| 5,607,431 A | 3/1997 | Dudasik |
| 5,643,271 A | 7/1997 | Sederholm et al. |
| 5,645,607 A | 7/1997 | Hickey |
| 5,653,714 A | 8/1997 | Dietz et al. |
| 5,658,349 A | 8/1997 | Brooks |
| 5,683,395 A | 11/1997 | Mikhail |
| 5,697,932 A | 12/1997 | Smith |
| 5,702,487 A | 12/1997 | Averill |
| 5,728,128 A | 3/1998 | Crickenberger |
| 5,743,915 A | 4/1998 | Bertin et al. |
| 5,752,972 A * | 5/1998 | Hoogeboom ............ 606/205 |
| 5,755,803 A | 5/1998 | Haines et al. |
| 5,766,261 A | 6/1998 | Neal |
| 5,769,855 A | 6/1998 | Bertin et al. |
| 5,776,200 A | 7/1998 | Johnson |
| 5,792,143 A | 8/1998 | Samuelson |
| 5,810,827 A | 9/1998 | Haines et al. |
| 5,810,829 A | 9/1998 | Elliott |
| 5,810,830 A | 9/1998 | Noble |
| 5,853,415 A | 12/1998 | Bertin et al. |
| 5,858,020 A | 1/1999 | Johnson |
| 5,860,969 A | 1/1999 | White |
| 5,860,981 A | 1/1999 | Bertin et al. |
| 5,876,459 A | 3/1999 | Powell |
| 5,879,354 A | 3/1999 | Haines et al. |
| 5,879,391 A | 3/1999 | Slamin |
| 5,906,644 A | 5/1999 | Powell |
| 5,908,423 A | 6/1999 | Kashuba et al. |
| 5,919,195 A | 7/1999 | Wilson |
| 5,935,172 A | 8/1999 | Ochoa |
| 5,951,606 A | 9/1999 | Burke |
| 5,957,925 A | 9/1999 | Cook et al. |
| 5,968,049 A | 10/1999 | Rold |
| 5,976,145 A | 11/1999 | Kennefick, III |
| 5,976,147 A | 11/1999 | LaSalle |
| 5,976,188 A | 11/1999 | Dextradeur |
| 5,993,455 A | 11/1999 | Noble |
| 6,045,556 A | 4/2000 | Cohen |
| 6,056,754 A | 5/2000 | Haines et al. |
| 6,071,311 A | 6/2000 | O'Neil |
| 6,080,162 A | 6/2000 | Dye |
| 6,090,146 A | 7/2000 | Rozow, III |
| 6,117,138 A | 9/2000 | Burrows |
| 6,120,507 A | 9/2000 | Allard et al. |
| 6,126,694 A | 10/2000 | Gray, Jr. |
| 6,159,214 A | 12/2000 | Michelson |
| 6,162,226 A | 12/2000 | DeCarlo, Jr. |
| 6,179,877 B1 | 1/2001 | Burke |
| 6,193,759 B1 | 2/2001 | Ro |
| 6,197,064 B1 | 3/2001 | Haines et al. |
| 6,197,065 B1 | 3/2001 | Martin et al. |
| 6,206,884 B1 | 3/2001 | Masini |
| 6,224,605 B1 | 5/2001 | Anderson |
| 6,238,435 B1 | 5/2001 | Meulink |
| 6,258,093 B1 | 7/2001 | Edwards |
| 6,258,095 B1 | 7/2001 | Lombardo |
| 6,258,097 B1 | 7/2001 | Cook |
| 6,270,502 B1 | 8/2001 | Stulberg |
| 6,287,342 B1 | 9/2001 | Copf et al. |
| 6,318,651 B1 | 11/2001 | Spiering |
| 6,319,286 B1 | 11/2001 | Fernandez |
| 6,332,886 B1 | 12/2001 | Green |
| 6,355,068 B1 | 3/2002 | Doubler |
| 6,361,563 B2 | 3/2002 | Terrill Grisoni |
| 6,432,110 B1 | 8/2002 | Richelsoph |
| 6,432,141 B1 | 8/2002 | Stocks et al. |
| 6,440,139 B2 | 8/2002 | Michelson |
| 6,508,841 B2 | 1/2003 | Martin |
| 6,517,581 B2 | 2/2003 | Blamey |
| RE38,058 E | 4/2003 | Fallin |
| 6,589,285 B2 | 7/2003 | Penenberg |
| 6,663,616 B1 | 12/2003 | Roth et al. |
| 6,676,706 B1 | 1/2004 | Mears et al. |
| 6,692,530 B2 | 2/2004 | Doubler |
| 6,702,854 B1 | 3/2004 | Cheal |
| 6,740,090 B1 | 5/2004 | Cragg |
| 6,770,100 B2 | 8/2004 | Draenert |
| 6,824,552 B2 | 11/2004 | Robison |
| 6,846,314 B2 | 1/2005 | Shapira |
| 6,875,218 B2 | 4/2005 | Dye |
| 6,949,101 B2 | 9/2005 | McCleary et al. |
| 7,001,392 B2 | 2/2006 | McGovern |
| 7,008,420 B2 | 3/2006 | Okada |
| 7,074,224 B2 | 7/2006 | Daniels |
| 7,641,658 B2 | 1/2010 | Shaolian |
| 2001/0001121 A1 | 5/2001 | Lombardo |
| 2001/0007957 A1 | 7/2001 | Martin |
| 2001/0016779 A1 | 8/2001 | Lubinus |
| 2001/0034526 A1 | 10/2001 | Kuslich |
| 2002/0183758 A1 | 12/2002 | Middleton |
| 2003/0093080 A1 | 5/2003 | Brown |
| 2003/0109882 A1 | 6/2003 | Shirado |
| 2003/0114933 A1 | 6/2003 | Bouttens |
| 2003/0130740 A1 | 7/2003 | Stocks et al. |
| 2003/0171756 A1 | 9/2003 | Fallin et al. |
| 2003/0171816 A1 | 9/2003 | Scifert |
| 2003/0187449 A1 | 10/2003 | McCleary et al. |
| 2003/0204269 A1 | 10/2003 | Gerbec |
| 2003/0220698 A1 | 11/2003 | Mears et al. |
| 2004/0015239 A1 | 1/2004 | Le Beguec |
| 2004/0054419 A1 | 3/2004 | Serra |
| 2004/0064186 A1 | 4/2004 | McCleary |
| 2004/0092951 A1 | 5/2004 | Serra et al. |
| 2004/0122437 A1 | 6/2004 | Dwyer |
| 2004/0122440 A1 | 6/2004 | Daniels |
| 2004/0122525 A1 | 6/2004 | Daniels |
| 2004/0147933 A1 | 7/2004 | McGovern |
| 2004/0172138 A1 | 9/2004 | May |
| 2004/0267266 A1 | 12/2004 | Daniels |
| 2004/0267267 A1 | 12/2004 | Daniels |
| 2004/0267372 A1 | 12/2004 | Vanasse |
| 2005/0004679 A1 | 1/2005 | Sederholm |
| 2005/0154331 A1* | 7/2005 | Christie et al. ............ 601/2 |

| | | | |
|---|---|---|---|
| 2005/0222572 A1 | 10/2005 | Chana | |
| 2005/0234461 A1 | 10/2005 | Burdulis | |
| 2006/0015110 A1 | 1/2006 | Pepper | |

FOREIGN PATENT DOCUMENTS

| | | |
|---|---|---|
| EP | 0206777 A2 | 12/1986 |
| EP | 0661023 | 12/1994 |
| EP | 1084680 | 12/1994 |
| EP | 0726063 | 8/1996 |
| EP | 0595956 | 9/1998 |
| EP | 861635 A2 | 9/1998 |
| EP | 0511244 | 10/1998 |
| EP | 861635 A3 | 11/1998 |
| EP | 1201191 A1 | 5/2002 |
| EP | 861635 B1 | 7/2002 |
| EP | 1263334 A2 | 12/2002 |
| EP | 1348384 | 3/2003 |
| EP | 1323395 A2 | 7/2003 |
| EP | 1369089 | 12/2003 |
| EP | 0842639 | 2/2004 |
| EP | 1493407 A2 | 1/2005 |
| EP | 1263334 B1 | 10/2005 |
| EP | 1591084 A1 | 11/2005 |
| FR | 2737107 A1 | 1/1997 |
| FR | 2828397 A1 | 2/2003 |
| GB | 2250441 A | 6/1992 |
| JP | 03339724 A | 12/2003 |
| WO | WO9110408 | 7/1991 |
| WO | WO9210138 | 6/1992 |
| WO | WO 9301769 A1 | 2/1993 |
| WO | WO9412123 | 6/1994 |
| WO | WO 9427507 A1 | 12/1994 |
| WO | WO 9815739 A1 | 4/1998 |
| WO | WO02102254 | 12/2002 |
| WO | WO 03015642 A1 * | 2/2003 |
| WO | WO 03065906 A2 | 8/2003 |
| WO | WO03082159 | 10/2003 |
| WO | WO 03092513 A1 | 11/2003 |
| WO | WO03094698 | 11/2003 |
| WO | WO 03094803 A1 | 11/2003 |

OTHER PUBLICATIONS

European Search Report From Corresponding Application No. 09168260, Dated Jan. 13, 2010, 7 Pages.

Paul, H. A., et al. "Development of a Surgical Robot for Cementless Total Hip Arthroplasty." Clinical Orthopedics and Related Research 285 Dec. 1992: 57-66.

Depuy Orthopaedics, Inc., "S-ROM Modular Hip System, Minimally Invasive Calcar Miller Surgical Technique", 0612-04-503, 2004, DePuy Orthopaedics, Inc.

European Search Report for EPO Application No. 09168260, Dated Jan. 13, 2010, 7 Pages.

* cited by examiner

MINIMALLY INVASIVE BONE MILLER APPARATUS

TECHNICAL FIELD OF THE INVENTION

This invention relates to the field of artificial joint prostheses and, in particular, to an improved instrument for machining a precise cavity in bone for receiving a prosthesis.

BACKGROUND OF THE INVENTION

For implantation of prosthetic stems, such as hip stems, accurate preparation of the bone or intramedullary canal is extremely important in order to guarantee good contact between the prosthesis stem and the bone. The underlying concept behind precise preparation is that a precise bone envelope reduces the gaps between the implant (i.e. prosthesis or prosthetic component) and the bone, thereby improving the initial and long-term bone ingrowth/fixation. The bone canal is presently prepared for implantation of a prosthetic stem by drilling and reaming a resected end of a bone, such as a femur, and then preparing an area adjacent the drilled hole to provide a seat for the prosthetic stem or a proximal sleeve coupled to the stem of a modular prosthetic system.

Modular prosthetic systems using proximal sleeves, stems, necks and heads, such as the S-ROM Modular Hip System, available from DePuy Orthopaedics, Warsaw, Ind., put more control in the hands of the surgeon, providing solutions for a variety of surgical scenarios, from primary total hip arthroplasty (THA) to the complex revision or DDH challenges. Such system provides such versatility because the provided plurality of stems, sleeves, necks and heads which can be assembled in a large number of configurations.

Preparation of the area adjacent the drilled hole may be accomplished by broaching or by milling. Broaches or rasps, when used for bone preparation, have limitations. One such limitation is the risk of fracture during broaching. Since broaching is done by pounding the broach into the bone, the bone tends to fracture. Additionally, both broaches and rasps suffer from a tendency to be deflected by harder sections of bone so that they do not create as precise a triangular cavity as can be created by a miller system. In a study that compared an intimate fill with robotically machined femoral, Paul et al., found that broaching tore the trabecular bone, whereas femoral canal preparation with reamers was consistently more accurate. Paul, H. A., et al. "Development of a Surgical Robot for Cementless Total Hip Arthroplasty." Clinical Orthopedics and Related Research 285 December, 1992: 57-66.

Thus, milling is currently the preferred method of bone preparation in many orthopaedic applications because it is an extremely precise method of bone preparation. A limitation of milling systems today is that they are typically formed so that the drive shaft extends at an angle relative to the remainder of the frame from the end of the miller cutter machining the bone. A fairly large incision must be made to accommodate such milling assemblies. A typical incision for preparing a femur for a total prosthetic hip replacement using a standard triangle miller system is eight to ten inches long. It is not uncommon for incisions as large as 12 inches to be used in a total hip replacement procedure.

A standard triangle miller system typically includes a miller shell, a miller frame and a miller cutter having an end formed for coupling to a drill. A typical miller frame and miller cutter can be seen in U.S. Pat. No. 5,540,694 issued to DeCarlo, Jr. et al. on Jul. 30, 1996. This miller frame allows for precise machining of the triangular canal by a miller cutter held at an angle with respect to the shaft of the frame. The triangular canal facilitates an accurate fit of a proximal sleeve that distributes the load experienced by the prosthesis evenly and provides rotational stability. However, to accommodate this miller, it is necessary to make a fairly large incision which may be undesirable for cosmetic or other reasons.

The large incision is required because the miller cutter includes a fixed input shaft for connecting to and/or receiving motive (i.e. rotary) power from a drill or similar instrument. As such, the prior reamer is able to accept rotary input power with respect to only one direction. Typically, this direction is at 0° (i.e. "straight on") with respect to the reamer which is approximately thirty two degrees with respect to the shaft of the miller frame. Therefore, not only is the input power direction restricted, but this, in turn, restricts the angle at which the reamer may be used on a patient. Since the input shaft and the drill coupled thereto extend laterally beyond the edge of the miller frame an incision substantially larger than the width of the frame must be made to accommodate the reamer, frame and drill during surgery. The incision must be large enough to accommodate the reamer, frame, input shaft and drill without the input shaft engaging soft tissue.

Recently, there have been some millers developed for minimally invasive surgery, however, they still require an incision of about three inches. However, as other instruments only require about one and a half to two inches, it is not ideal to use a miller that requires a larger incision.

In view of the above, it would be desirable to have a bone miller or guided reamer that could fit into a smaller incision during a surgical process.

SUMMARY OF THE INVENTION

According to one embodiment of the present invention, a miller assembly for creating a cavity in a bone is provided. The cavity has a cross section which has a generally triangular profile having a first side generally parallel with an axis of the bone and a second side forming an acute angle with the first side, and is contiguous with a pre-existing conical cavity in the bone. The assembly includes a cutter and a frame for carrying the cutter. The frame includes a connection portion having a longitudinal axis and a cutter mount for mounting the cutter at a first angle approximating the acute angle with respect to the longitudinal axis of the connection portion. The cutter mount extends at the first angle from the longitudinal axis of the connection portion and is configured to receive a portion of the cutter and maintain the received cutter oriented at the first angle during rotation. The frame further includes a handle configured to form a portion of a drive joint for coupling the frame to a drill, the handle having a longitudinal axis. The longitudinal axis of the handle is coincident with the longitudinal axis of the frame.

According to another embodiment of the present invention, a miller assembly for creating a cavity in a bone is provided. The system includes a cutter and a frame for carrying the cutter. The frame has a longitudinal axis and a cutter mount for mounting the cutter at a first angle with respect to the longitudinal axis of the frame. The cutter mount extends at the first angle from the longitudinal axis of the frame and is configured to receive a portion of the cutter and to maintain the received cutter oriented at the first angle during rotation. The frame further includes a handle configured to form a portion of a drive joint for coupling the frame to a drill having a longitudinal axis. The handle has a longitudinal axis, such that the longitudinal axis of the handle is coincident with the longitudinal axis of the frame. The cutter is coupled to the connection portion and handle such that when the drill is activated, the cutter rotates.

According to yet another embodiment of the present application, a method of milling a calcar region of the femur is provided. The method including providing a miller assembly including a cutter and a frame for carrying the cutter. The frame has a longitudinal axis and a cutter mount for mounting the cutter at a first angle with respect to the longitudinal axis of the frame. The cutter mount extends at the first angle from the longitudinal axis of the frame and is configured to receive a portion of the cutter and to maintain the received cutter oriented at the first angle during rotation. The frame further includes a handle configured to form a portion of a drive joint for coupling the frame to a drill, the handle having a longitudinal axis. The handle is coupled to the drill. The miller assembly is inserted into the femur such that the cutter is located in the calcar region. The drill is then operated, causing the cutter to rotate and mill bone in the calcar region

BRIEF DESCRIPTION OF THE DRAWINGS

For a more complete understanding of the present invention and the advantages thereof, reference is now made to the following description taken in connection with the accompanying drawings, in which.

Corresponding reference characters indicate corresponding parts throughout the several views. Like reference characters tend to indicate like parts throughout the several views.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
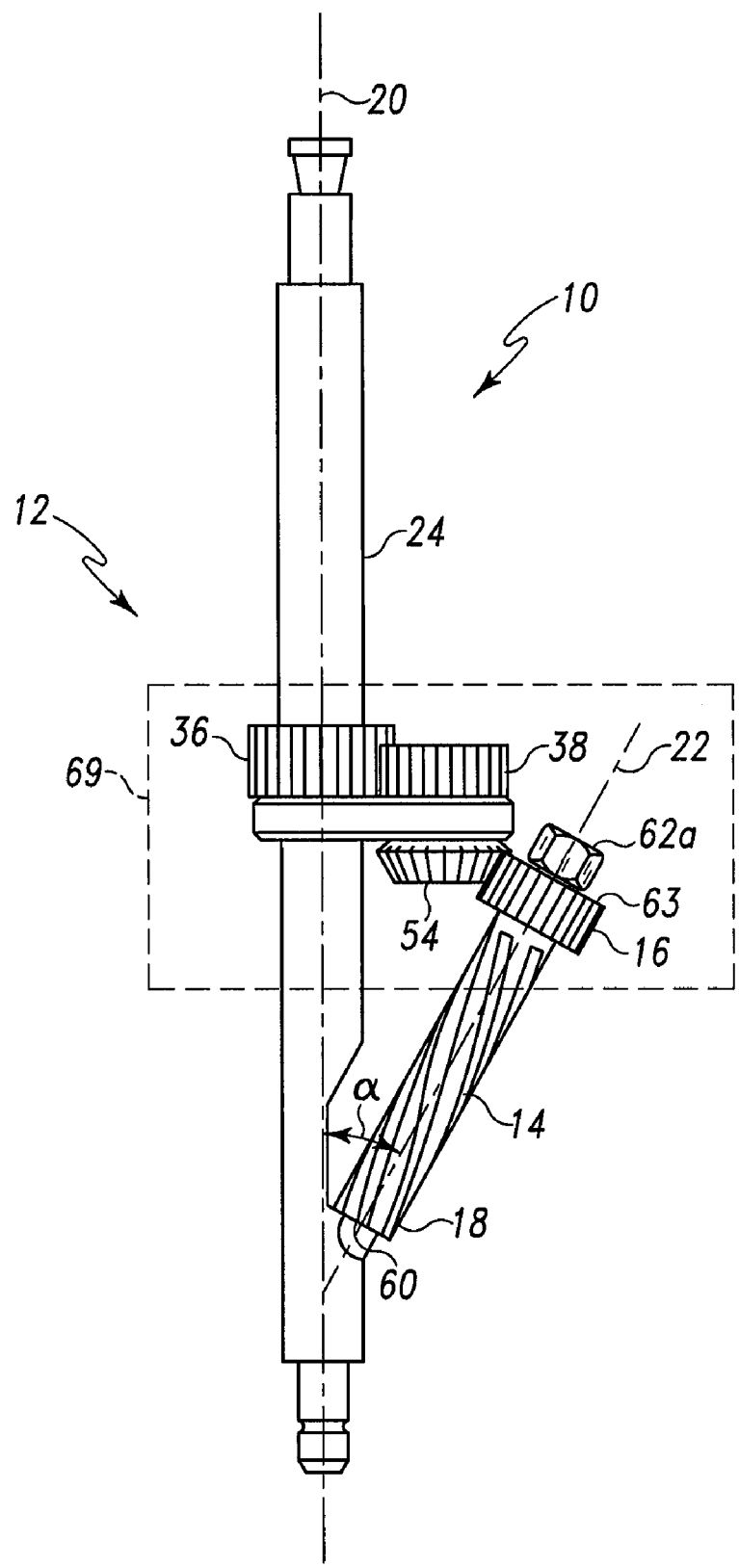
FIG. 1 is a perspective view of a miller system according to one embodiment of the present invention.

The disclosed calcar miller assembly 10 allows a surgeon to machine (mill) bone through a smaller incision compared to existing surgical instruments. As shown in FIG. 1, the miller assembly 10 includes a frame 12 and a miller cutter 14 that is coupled to the frame 12 at both a proximal end 16 and a distal end 18. The frame 12 includes a longitudinal axis 20. The miller cutter 14 also has a longitudinal axis 22 that is offset at an angle α from the longitudinal axis 20 of the frame 12. The angle α is greater than 0 degrees. In some embodiments, the angle α is between about 30 and about 60 degrees. In some embodiments, the angle α is between about 40 degrees and about 50 degrees.

Figure 2:
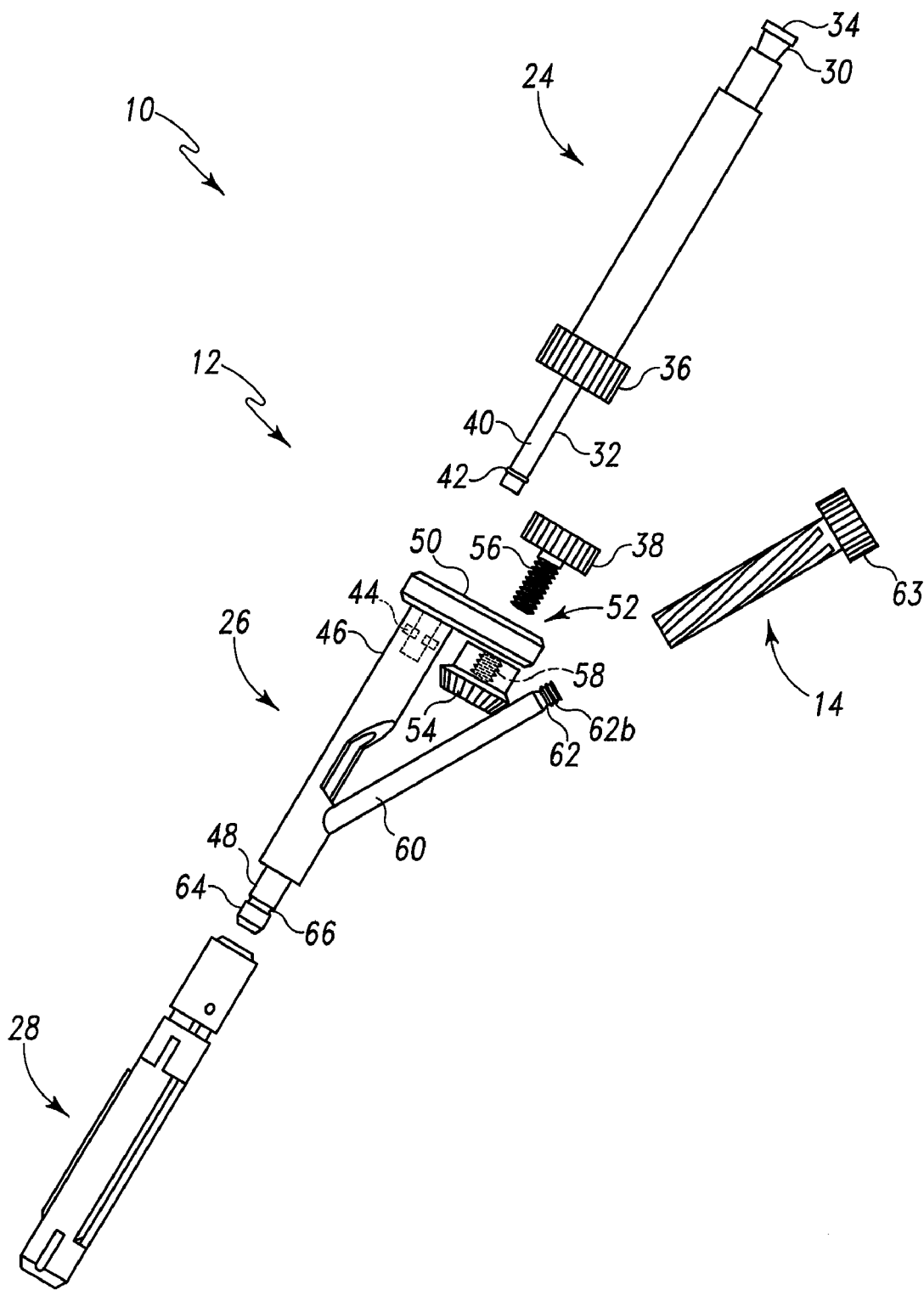
FIG. 2 is an exploded view of the miller system of FIG. 1.

Turning now to FIG. 2, an exploded view of the calcar miller assembly 10 of FIG. 1 is illustrated. As shown, the frame 12 includes three parts: a handle 24, a connection portion 26, and a pilot shaft 28. The handle 24 includes a drill-connection end 30 and a connection-portion end 32. The drill-connection end 30 includes a drill-connection feature 34 adapted to connect the handle to a drill (not shown), creating a drive joint. The drill will drive the miller cutter 14. In this embodiment, the handle 24 also becomes the drive shaft, such that the longitudinal axis of the handle is coincident with the longitudinal axis of the drive shaft.

The connection-portion end 32 of the handle 24 includes a gear 36 that will couple with a gear 38 of the connection portion 26, as will be described in more detail below. The connection-portion end 32 of the handle 24 also includes a rod 40, for connecting the handle 24 to the connection portion 26. The rod 40 includes a locking mechanism 42 that corresponds to a locking mechanism 44 (shown in phantom) on the connection portion 26. The rod and connection portion locking mechanisms 42, 44 may include a recess on one and an internal ridge on the other. Other locking mechanisms, including, but not limited to, threads, tapers, locking bulbs, and locking tabs, may be used. Also, the pieces may be welded together.

Also, in other embodiments, the rod 40 may be located on the connection portion 26. The rod 40 would engage a cavity in the handle 24.

The connection portion 26 includes a handle-connection end 46 and a shaft-connection end 48. The handle-connection end 46 couples to the handle 24 as described above. The handle-connection end 46 includes an outwardly extending flange 50. The flange 50 includes a recess 52 for receiving the gear 38. The gear 38 couples to a lower gear 54 via a thread 56 on the gear 38 that matingly engages an internal thread 58 (as shown in phantom) on the lower gear 54. The miller cutter 14 slides onto a cutter mount, or an outwardly extending pole 60. The pole 60 extends at the desired angle α as described and shown above in reference to FIG. 1. The outwardly extending pole 60 includes a locking mechanism 62, which in the illustrated embodiment, is a nut 62a (FIG. 1) and a threads 62b on the pole 60. Alternatively, other locking mechanisms such as taper locks, locking bulbs, locking tabs and other known locking mechanisms may be used. The miller cutter 14 also includes a gear 63 that will mate with the lower gear 54. Also, the pieces may be welded together.

Figure 3:
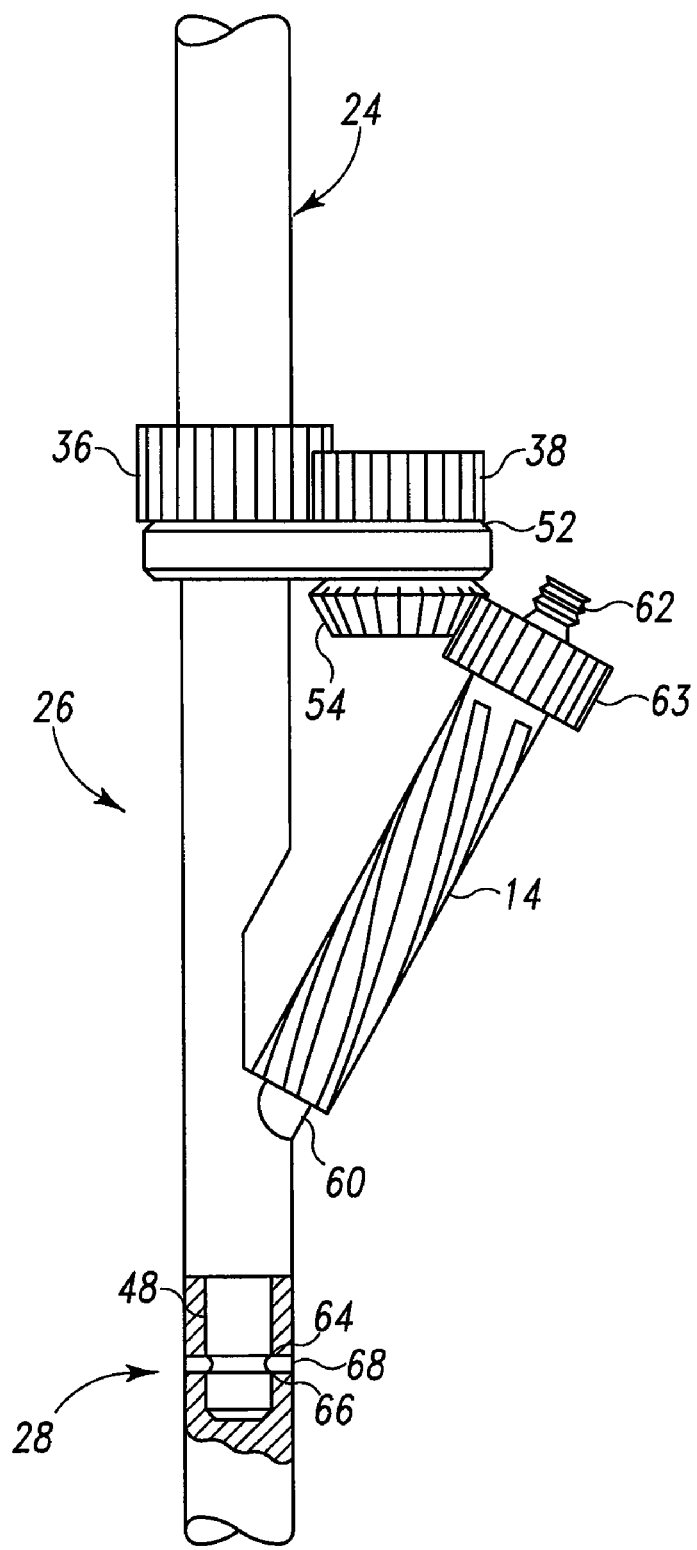
FIG. 3 is a perspective view of the miller frame of FIG. 1 illustrating the mating of the gears.

The shaft-connection end 48 of the connection portion 26 includes a locking mechanism 64 for locking the connection portion 26 to the shaft 28. As shown, the locking mechanism 64 includes a recess 66 which will engage an internal ridge 68 (shown in FIG. 3) on the shaft 28. Other locking mechanisms, including, but not limited to, threads, tapers, locking bulbs, and locking tabs, may be used. In other embodiments, the pieces may be welded together.

In an alternative embodiment, the shaft 28 will be connected to a miller shell (not shown). The handle 24 and connection portion 26 will slide into the miller shell. The handle 24/connection portion 26 can be moved up and down relative to the miller shell in order to adjust the depth of the drilling.

Returning now to FIG. 1, a shroud 69 is shown in phantom. In some embodiments, the shroud 69 may be included to cover the gears 36, 38, 54, 63. The shroud 69 would be to protect the gears 36, 38, 54, 63 during the surgery. Also, the shroud 69 could keep the gears 36, 38, 54, 63 from engaging the bone and/or soft tissue.

Figure 4:
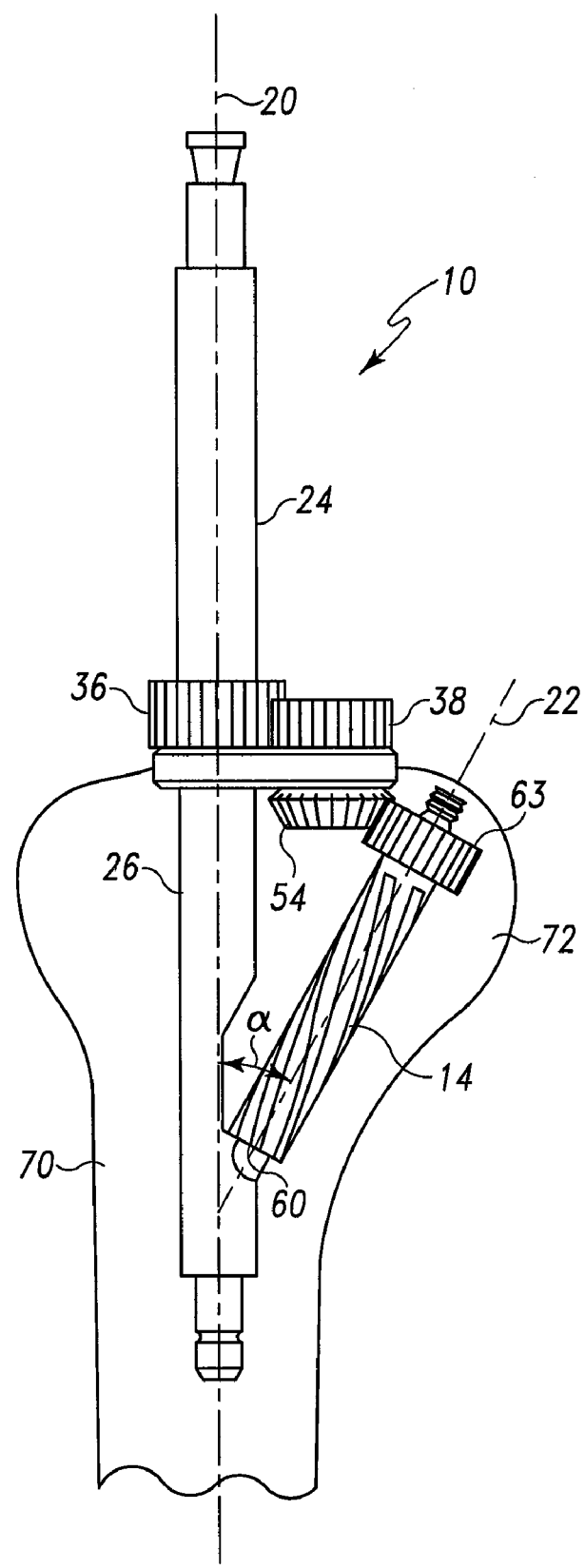
FIG. 4 is a perspective view with parts broken away of the miller system of FIG. 1 inserted into a resected femur of a patient.

Turning now to FIG. 4, a perspective view of the connection portion 26 with the miller cutter 14 placed on the pole 60 is shown. The connection portion 26 is shown in a femur 70, with the miller cutter 14 located in the calcar region 72. As shown, the handle gear 36 will rotate with the handle 24. As the handle gear 36 is rotated, it will engage the top connection portion gear 38 to rotate, causing the bottom connection gear 54 to rotate. The bottom connection gear 54 is engaged with the miller cutter gear 63 such that when the bottom connection gear 54 rotates, so does the miller cutter gear 63. As the miller cutter gear 63 rotates, so do the blades of the miller cutter 14 about the axis 22 of the rod 60. The result is that the calcar region 72 is milled in preparation for receiving an implant.

Figure 5:
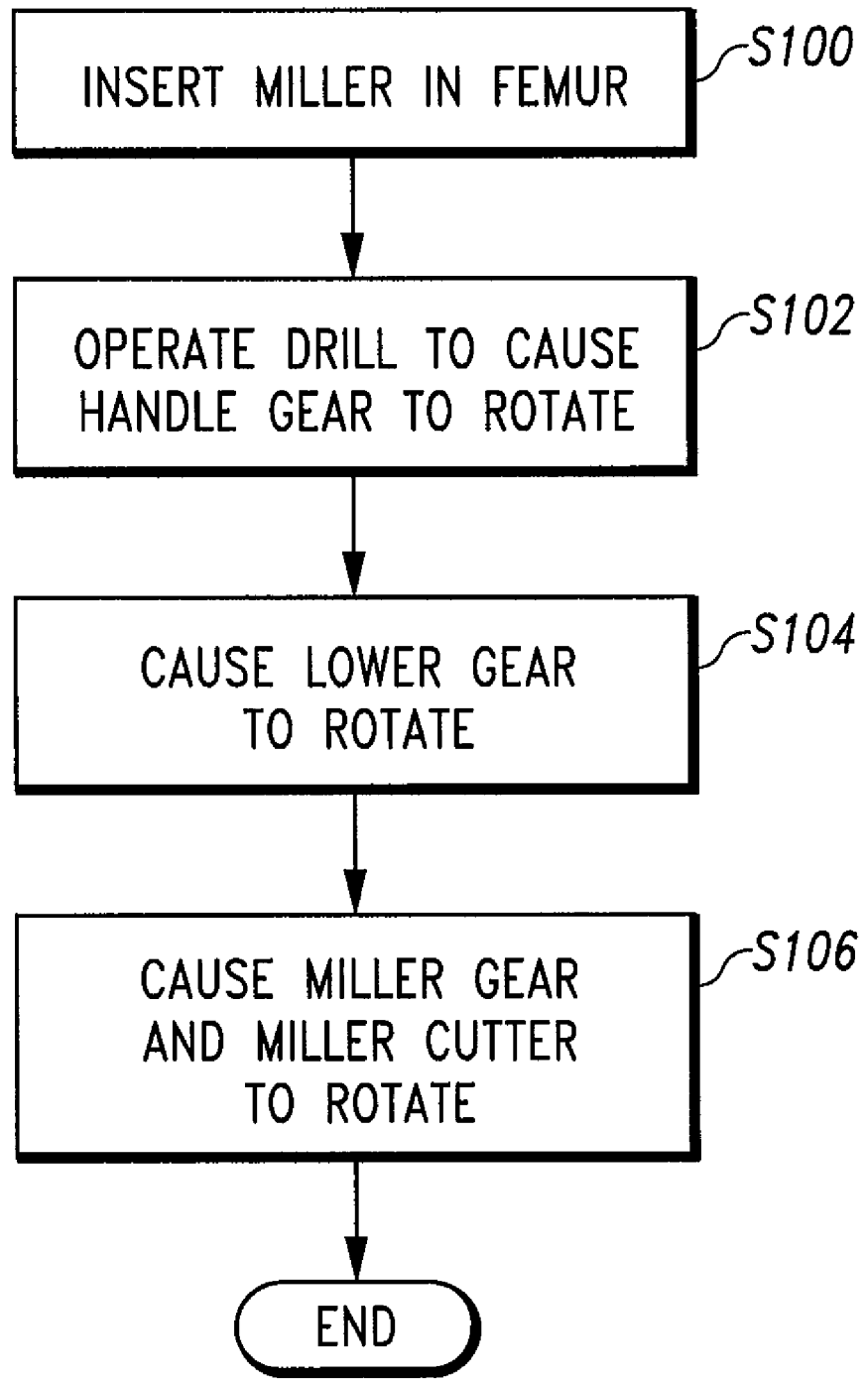
FIG. 5 is a flow chart describing a method of using the miller of FIG. 1.

Turning now to FIG. 5, a flow chart describing the operation of the miller 10 will be described. First, at step s100, the miller will be inserted into the femur 70, with the miller cutter 14 being inserted into the calcar region 72. At step s102, the drill causes the handle 24 and handle gear 36 rotate. The rotation of the handle gear 36 causes the lower gear 54 to rotate (step s104), which in turn drives the rotation of the miller cutter 14 (step s106). The miller cutter 14 then mills the bone in the calcar region 72 of the femur 70, preparing the calcar region for the insertion of the implant.

In some embodiments, the miller 10 can be inserted into a miller shell (not shown). The miller shell is inserted into the femur and the miller 10 can be adjusted vertically so as to adjust the cutting depth.

Figure 6:
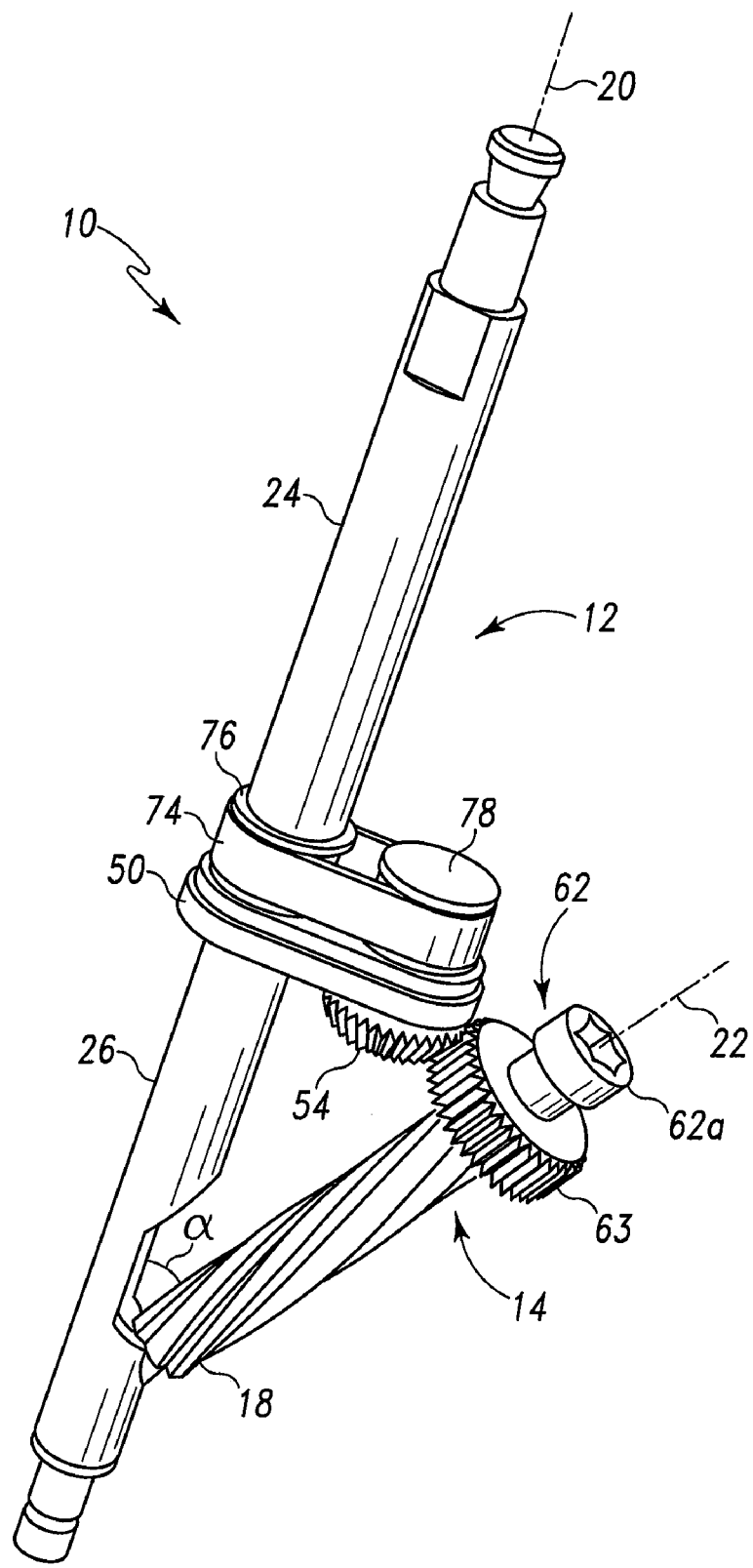
FIG. 6 is a perspective view of a miller system according to another embodiment of the present invention.

Turning now to FIG. 6, a second embodiment of the present invention is illustrated. In this embodiment, the handle 24 of the miller assembly 10 is coupled to the connection portion 26 via a belt 74. As shown, the belt 74 winds around a cylinder 76 located on the handle 24 and a cylinder 78 on the flange 50. The cylinder 78 on the flange is coupled to the bottom connection gear 54 in the same way that the top connection gear 38 is coupled to the bottom connection gear 54 in the above-described embodiment. As the handle 24 is rotated, the cylinder 76 rotates, causing the belt 74 to move. The movement of the belt 74 then causes the cylinder 78 of the flange to rotate, rotating the upper gear 38 and bottom connection gear 54. Then, in the same manner as described above, the bottom connection gear 54 then couples with the cutter gear 63.

In some embodiments, the miller cutter assembly 10 is made of stainless steel or other biocompatible metal, such as titanium or cobalt chrome. Any other sterilizable metal may be used. In other embodiments, the handle 24, connection portion 26, and pilot shaft may be disposable and made of a biocompatible plastic such as polycarbonate, LEXAN®, ULTEM®, both manufactured by Sabic Innovation Plastics of Houston, Tex., CELCON®, manufactured by Ticona of Florence, Ky., UDEL®, RADEL®, ACUDEL®, MINDEL®, Epispire, Primospire, TORLON®, all manufactured by Solvay Plastics of Brussels, or any other biocompatible plastic, while the miller cutter 14 is made of stainless steel or other sterilizable metal.

In the embodiments shown and described in reference to FIGS. 1-6, the width of the device is less than about 2 and one half inches, and in some embodiments, less than about 2 inches. By coupling the handle to the drive shaft directly, the surgical opening can be smaller than other current designs.

In the above described embodiments, the frame 12 was in three parts. However, in alternative embodiments, the frame may be a single piece or may have more or less than three parts.

Although specific embodiments of the invention have been described herein, other embodiments may be perceived by those skilled in the art without departing from the scope of the invention as defined by the following claims. For example, although the invention has been described in terms of the implantation of the femoral portion of a hip prosthesis, it can be used with prostheses for other joints such as the shoulder, knee, or elbow.

We claim:

1. A miller assembly for creating a cavity in a bone, the cavity (i) having a cross section which has a generally triangular profile having a first side generally parallel with an axis of the bone and a second side forming an acute angle with the first side, and (ii) being contiguous with a pre-existing conical cavity in the bone, the assembly comprising:
    a cutter; and
    a frame for carrying the cutter, the frame including (i) a connection portion having a longitudinal axis, (ii) a laterally extending flange adapted to operationally couple a proximal end of the cutter to the connection portion, in which the flange includes a top gear on the top of the flange, and (iii) a cutter mount for mounting the cutter at a first angle approximating the acute angle with respect to the longitudinal axis of the connection portion, the cutter mount extending at the first angle from the longitudinal axis of the connection portion and configured to receive a portion of the cutter and maintain the received cutter oriented at the first angle during rotation, and the frame further including a handle configured to form a portion of a drive joint for coupling the frame to a drill, the handle having a longitudinal axis; wherein the longitudinal axis of the handle is coincident with the longitudinal axis of the connection portion, wherein the flange includes a bottom gear that engages the top gear on the flange, such that the bottom gear rotates when the top gear is rotated; wherein the handle includes a gear at a distal end, the gear of the handle being coupled to the top gear; wherein the cutter includes a gear that engages the bottom gear; and wherein the connection portion and the cutter are fully inserted in the bone after the connection portion is inserted into the pre-existing conical cavity in the bone.

2. The miller assembly of claim 1, wherein the frame further includes a pilot shaft.

3. The miller assembly of claim 2, wherein the pilot shaft, connection portion, and handle are removably coupled to one another.

4. The miller assembly of claim 3, wherein the pilot shaft includes a locking mechanism adapted to lockingly engage a corresponding shaft-locking mechanism on the connection portion.

5. The miller assembly of claim 3, wherein the handle includes a locking mechanism adapted to lockingly engage a corresponding handle-locking mechanism on the connection portion.

6. A miller assembly for creating a cavity in a bone, the system comprising:
    a cutter; and
    a frame for carrying the cutter, the frame having a connection portion having a longitudinal axis and a cutter mount for mounting the cutter at a first angle approximating an acute angle with respect to the longitudinal axis of the connection portion, the cutter mount extending at the first angle from the longitudinal axis of the connection portion and configured to receive a portion of the cutter and maintain the received cutter oriented at the first angle during rotation, and the frame further including a handle configured to form a portion of a drive joint for coupling the frame to a drill, the handle having a longitudinal axis; wherein the longitudinal axis of the handle is coincident with the longitudinal axis of the connection portion, the cutter being coupled to the connection portion and handle such that when the drill is activated, the cutter rotates, wherein the connection portion includes a gear assembly including a top gear and a bottom gear, the top gear coupled to the bottom gear such that when the top gear is rotated, the bottom gear rotates; wherein the handle includes a gear at a distal end, the gear of the handle being coupled to the top gear; wherein the cutter includes a gear that engages the bottom gear; and wherein the connection portion and the cutter are fully inserted in the bone after the connection portion is inserted into a pre-existing conical cavity in the bone.

7. The miller assembly of claim 6, wherein the frame further includes a pilot shaft, the pilot shaft and connection portion having a locking mechanism for locking the pilot shaft to the connection portion.

8. The miller assembly of claim 7, wherein the locking mechanism includes a ring on one of the pilot shaft and the connection portion and a recess for engaging the ring on the other of the pilot shaft and the connection portion.

9. The miller assembly of claim 7, wherein the cutter is a cannulated cutter that slides over the cutter mount at the first angle.

10. The miller assembly of claim 9, wherein the locking mechanism includes a threaded screw on one of the handle and the connection portion and a threaded recess for engaging the threaded screw on the other of the handle and the connection portion.

* * * * *